United States Patent [19]

Tsilibary

[11] Patent Number: 5,152,784
[45] Date of Patent: Oct. 6, 1992

[54] PROSTHETIC DEVICES COATED WITH A POLYPEPTIDE WITH TYPE IV COLLAGEN ACTIVITY

[75] Inventor: Photini-Effie C. Tsilibary, Minneapolis, Minn.

[73] Assignee: Regents of the University of Minnesota, Minneapolis, Minn.

[21] Appl. No.: 704,055

[22] Filed: May 22, 1991

Related U.S. Application Data

[62] Division of Ser. No. 450,861, Dec. 14, 1989.

[51] Int. Cl.$^5$ ............ A61F 2/06; A61F 2/16; A61F 2/24; A61F 2/00
[52] U.S. Cl. ............................................ 623/1; 623/2; 623/3; 623/6; 623/11; 623/22; 623/23; 623/66; 435/240.23; 530/327; 514/14
[58] Field of Search ............ 530/326, 327; 623/1, 623/2, 3, 6, 11, 23, 66; 514/14

[56] References Cited

U.S. PATENT DOCUMENTS

| | | | |
|---|---|---|---|
| 4,578,079 | 3/1986 | Ruoslanti et al. | 623/11 |
| 4,870,160 | 9/1989 | Charonis et al. | 530/326 |
| 4,876,332 | 10/1989 | Tsilibary et al. | 530/326 |

OTHER PUBLICATIONS

Koliakos, et al., *J. of Biol. Chem.* vol. 264, (4) Feb. 5, 1989, pp. 2313-2323.
R. Timpl et al., *Macromolecular Organization of Type IV Collagen,* in New Trends in Basement Membrane Research, K. Kuehn et al. eds., Raven Press, NY, at 57-67 (1982).
J. Murray et al., *J. Cell Biol.,* 80, 197-202 (1979).
M. Aumailley et al., *J. Cell Biol.,* 103, 1569-1576 (1986).
T. Herbst et al., *J. Cell Biol.,* 106, 1365-1373 (1988).
M. Kurkinen et al., *J. Biol. Chem.,* 259, 5915-5922 (1984).
S. Sugrue, *J. Biol. Chem.,* 262, 3338-3343 (1987).
K. Tomaselli et al., *J. Cell Biol.,* 105, 2347-2358 (1987).
I. Oberbaumer et al., *Eur. J. Biochem.,* 147, 217-224 (1985).
T. Pihlajaniemi et al., *J. Biol. Chem.,* 260, 7681-7687 (1985).
U. Schwarz-Magdolen et al., *FEBS Lett.,* 208, 203-207 (1986).
D. Brazel et al., *Eur. J. Biochem.,* 172, 35-42 (1988).
R. Soininen et al., *FEBS Lett.,* 225, 188-194 (1987).
D. Brazel et al., *Eur. J. Biochem.,* 168, 529-536 (1987).
G. Muthukumaran et al., *J. Biol. Chem.,* 264, 6310-6317 (1989).
J. Saus et al., *J. Biol. Chem.,* 264, 6318-6324 (1989).
D. Shotton et al., *J. Mol. Biol.,* 131, 303-329 (1979).
W. Babel et al., *Eur. J. Biochem.,* 143, 545-556 (1984).
E. Tsilibary et al., *J. Cell Biol.,* 103, 2467-2473 (1986).
E. Tsilibary et al., *J. Biol. Chem.,* 263, 19112-19118 (1988).
M. Chelberg et al., *Cancer Research,* 49, 4796-4802 (1989).

*Primary Examiner*—Lester L. Lee
*Assistant Examiner*—S. G. Marshall
*Attorney, Agent, or Firm*—Merchant, Gould, Smith, Edell, Welter & Schmidt

[57] ABSTRACT

A polypeptide having the following formula is provided: gly-glu-phe-tyr-phe-asp-leu-arg-leu-lys-gly-asp-lys which can bind heparin and promote cellular adhesion.

Medical devices such as prosthetic implants, percutaneous devices and cell culture substrates coated with a composition including the polypeptide are also provided.

8 Claims, 10 Drawing Sheets

```
                             16
KPPGAMGPPGGEGPPGSSGPPGIKGEKGFPGFPGCLDMPGPKGDKGSQGLPGLTGQSGLPGLPGQQGTPGVPGFPGSKGDKGVMGTPGQPGSPGPAGTPG  900
||||||||||||| ||||||||||||||||||||||| ||||||||||||||||| ||||||||||| ||||| ||||||||||||||||| | ||
KPPGAMGPPGGQGPPGLSGPPGIKGEKGFPGFPGCLDMPGPKGDKGAQGLPGITGQSGLPGLPGQQGAPGIPGFPGSKGDKGVMGTPGQPGSPGPVGAPG  900

17
LPGEKGDEGLPGSSGPKGDPGFKGDKGDVGLPGKPGCSNEEVDMGSMEGQKGDQGEKGQIGPTGDKGSKGDPGTPGVPGKDGQAGEPGQPGPKGDPGLSGT 1000
||||||||| ||| |||||||||||||| ||||||| ||||||||||||||||||||| ||| ||||||||||||||||| ||| ||||||||||
LPGEKGDEGFPGSKGPKGDPGLKGDKGDVGLPGKPGCSMDKVDMGSMEGQKGDQGEKGQIGPIGEKGSKGDPGTPGVPGKDGQAGQPGQPGPKGDPGISGT 1000

18
PGSPGLPGPKGSVGGMGLPGSPGEKGVPGIPGSQGVPGSPGEKGAKGEKGQSGLPGIGIPGKPGDKGDQGLAGYPGSPGEKGEKGSAGTPGKPGSPGPRG 1100
|| |||||||||||||||||  || || |||||||||| |||||||||||||| ||||| |||||||||||||||||||||| ||| |||||| |
PGAPGLPGPPGSVGGMGLPGTPGEKGVPGIPGPQGSPGLPGDKGAKGEKGQAGPPGIGIPGLKGEKGDQGLAGYPGSPGEKGEKGSIGIPGKPGSPGLKG 1100

19
SPGNIGHPGSPGLPGEKGDKGLPGLDGVPGVKGEAGLPGTPGPTGPAGQKGEPGSDGIPGSAGEKGEQGVPGKGYPGFPGSKGDKGSKGEVGFPGLAGSP 1200
|||  ||||||||||||||||||||| |||||||||||||||||||||||||||||||||||||||||| | ||||||| ||||||||||||||||
SPGSVGYPGSPGLPGEKGDKGLPGLDGIPGVKGEAGLPGTPGPTGPAGQKGEPGSDGIPGSAGEKGEPGLAGYPGFPGAKGDKGSKGEVGFPGLAGSP 1200

20
GIPGVKGEQGPMGPPGPQGQPGLPGTPGEHWESPKGDRGPQGQPGLPGHPGPMGPPGFPGINGPKGDKGMQGMPGAPGVPGPKGDPGPQGMPGIGGSPGI 1300
|||| |||||||||||||||||||||||  |||||||||||||||||||||||||||||  ||||||||||||||||||||||||||||||||||
GIPGSKGEQGPMGPPGPQGQPGLPGSPGHATEGPKGDRGPQGQPGLPGLPGPMGPPGCLPGIDGVKGDKGMPGWPGAPGVPGPKGDPGPQGMPGIGGSPGI 1300

21
TGSKGDMGLPGVPGPQGQKGLPGLQGVKGDQGDQGVPGPKGLQGPPGPPGPFDVIKGEPGLPGPEGPPGLKGLQGPPGPKGQQGVTGSWGLPGPPGVPGF 1400
|||||||| ||||||||||||||| |||||||||||| |||||||||||| ||||||||||||||||||||||||||||||||| ||||||| |||
TGSKGDMGPPGVPGPQGPKGLPGLQGIKGDQGDQGVPGAKGLPGPPGPPGPFDIIKGEPGLPGPEGPPGLKGLQGLPGPKGQQGVTGLWGIPGPPGIPGF 1400

NC1
DGAPGQKGETGPPGPCGPPGTPGPGPDGLPGSNCPPGTPSVDEGFLVTRHSQTTDDPLCPPGTKILYEGYSLLYVQGNERAHGQDLGTAGSCLRKFSTH 1500
||||||||  || || ||||| |||||||||| |||||||||||||||||| |||| ||| |||||||||||||||||||||||||||||||||||
DGAPGQKGEMGPAGPTGPKGPPGPGPDGLPGSMCPPGTPSVDEGFLVTRHSQTIDDPQCPSGTKILYEGYSLLYVQGNERAHGQDLGTAGSCLRKFSTH 1500

PFLPGNIKWVGNPASRWDYSTWLSTPEPMPMSMAPISGDWIRPFISRCAVGEAPAWMAVESQTIQIPQCPWGKSSLWIGYSFVMHTSAGAEGSGQALAS 1600
|||||||||||||||||||||||||| ||||||||| |||||||||||||||| |||||||||||| ||| ||||||||||||||||||||||||
PFLPGNIKWVGNPASRWDYSTWLSTPEPMPMSMAPITGEWIRPFISRCAVGEAPAWMAVESQTIQIPPGPSGWSSLWIGYSFVMHTSAGAEGSGQALAS 1600

PGSGLEEFRSAPFIEGBGRGTGNYYAMAYSFWLATIEKSEMFKKPTPSTLKAGELRTHVSRCQVCHRKT 1699
|||||||||||||||||||||||||||||||||||||||||||||||||||||||||||||||||||
PGSCLEEFRSAPFIEGBGRGTGNYYAMAYSFWLATIEKSEMFKKPTPSTLKAGELRTHVSRCQVCHRKT 1699
```

PROSTHETIC DEVICES COATED WITH A POLYPEPTIDE WITH TYPE IV COLLAGEN ACTIVITY

GOVERNMENT SUPPORT

This invention was made with government support under contract No. DK 39216-02 by the U.S. Institutes of Health. The government has certain rights in the invention.

This is a division, of application Ser. No. 07/450,861, filed Dec. 14, 1989.

BACKGROUND OF THE INVENTION

Type IV collagen is a distinctive glycoprotein which occurs almost exclusively in basement membranes, structures which are found in the basal surface of many cell types, including vascular endothelial cells, epithelial cells, etc. Type IV collagen is a major component of basement membranes. It differs from interstitial collagens. See *New Trends in Basement Membrane Research*, K. Kuehn et al., eds., Raven Press, NY, at pp. 57-67 (1982). Type IV collagen has a molecular weight (MW) of about 500,000 and consists of three polypeptide chains: two $\alpha 1$ (MW 185,000) chains and one $\alpha 2$ (MW 170,000) chain. Type IV collagen has two major proteolytic domains: a large, globular, non-collagenous, NC1 domain and another major triple-helical collagenous domain. The latter domain is often interrupted by non-collagenous sequences of variable length. A diagrammatic representation of the type IV collagen molecule is shown in FIG. 1. It is a complex and multidomain protein with different biological activities residing in different domains.

Type IV collagen self-assembles to polymeric structures which constitute the supportive frame of basement membranes. Various other macromolecular components bind to type IV collagen, such as: laminin, entactin/nidogen and heparan sulfate proteoglycan. An additional function of type IV collagen is to mediate cell binding. A variety of cell types specifically adhere and spread onto type IV collagen-coated substrata. See J. C. Murray et al., *J. Cell Biol.*, 80, 197-202 (1979); M. Aumailley et al., *J. Cell Biol.*, 103, 1569-1576 (1986); T. J. Herbst et al., *J. Cell Biol.*, 106, 1365-1373 (1988). Various cell surface proteins, a 47 kD protein [M. Kurkinen et al., *J. Biol. Chem.*, 259, 5915-5922 (1984)], a 70 kD protein [S. P. Sugrue, *J. Biol. Chem.*, 262, 3338-3343 (1987)] and members of the superfamily of integrins [K. J. Tomaselli et al., *J. Cell Biol.*, 105, 2347-2358 (1987)], have been reported to mediate cell binding to type IV collagen.

The variety of functions of type IV collagen suggests that this glycoprotein is important in many diverse and clinically relevant processes such as cell attachment and migration, wound healing, tumor cell metastasis and invasion, diabetic microangiopathy, vascular hypertrophy due to hypertension and several kidney diseases such as diabetic nephropathy and nephrotic syndromes of variable etiology. For example, in Goodpasture's syndrome, a disease characterized by hemoptysis and hematuria due to alveolitis and nephritis, respectively, an antibody to the major non-collagenous NC1 domain of type IV collagen is found in the serum of all Goodpasture's patients. Another hereditary kidney disease, Alport's familial nephritis, is apparently due to a genetic defect of the NC1 domain of type IV collagen. In addition, in diabetes mellitus, intact type IV collagen, as well as the triple helix-rich domain, are chemically modified and functionally impaired by the increased amounts of glucose present in the plasma and in the immediate vicinity of the basement membranes, i.e., in the extracellular matrix.

In order to better understand the pathophysiology of these processes at a molecular level, there is a need to try to assign at least several of the above-mentioned biological activities of type IV collagen to the specific proteolytic domains (i.e., NC1, triple helix-rich domains) or oligopeptide of type IV collagen. If this can be achieved, it will be possible to synthesize small peptides which can provide the basis for important pharmaceutical compositions.

BRIEF DESCRIPTION OF THE INVENTION

The present invention provides a polypeptide (hereinafter designated "Hep-III") which represents a fragment of the $\alpha 1$ chain of type IV collagen. This polypeptide can be prepared by conventional solid phase synthesis. The formula of the polypeptide is:

gly-glu-phe-tyr-phe-asp-leu-arg-leu-lys-gly-asp-lys

Polypeptide Hep-III formally represents isolated type IV collagen residues 531-543 from the amino-terminus of the $\alpha 1$ chain of type IV collagen. The single letter amino acid code for this polypeptide is GE-FYFDLRLKGDK.

This synthetic polypeptide was assayed for biological activity and found to be an extremely potent promoter of heparin-binding to synthetic substrates. Polypeptide Hep-III was also a potent promoter of cell adhesion and spreading of many cell types, including melanoma and endothelial cells. Therefore, it is believed that polypeptide Hep-III may be useful to (a) promote cellular attachment to culture substrata, (b) inhibit the metastasis and invasion of malignant cells, and (c) promote wound healing and implant acceptance. Since other cell types have been shown or are expected to have similar behavior in response to Hep-III, other uses of peptide Hep-III could be envisioned, such as assistance in nerve regeneration. Furthermore, since it is expected that further digestion/hydrolysis of peptide Hep-III in vitro or in vivo will yield some fragments of substantially equivalent bioactivity, such lower molecular weight peptides are also considered to be within the scope of the present invention.

BRIEF DESCRIPTION OF THE DRAWINGS

FIG. 2 depicts the primary amino acid sequence of the human and murine $\alpha 1$ chain of type IV collagen in comparison. The sequence is highly conserved between these two species.

DETAILED DESCRIPTION OF THE INVENTION

Figure 2:
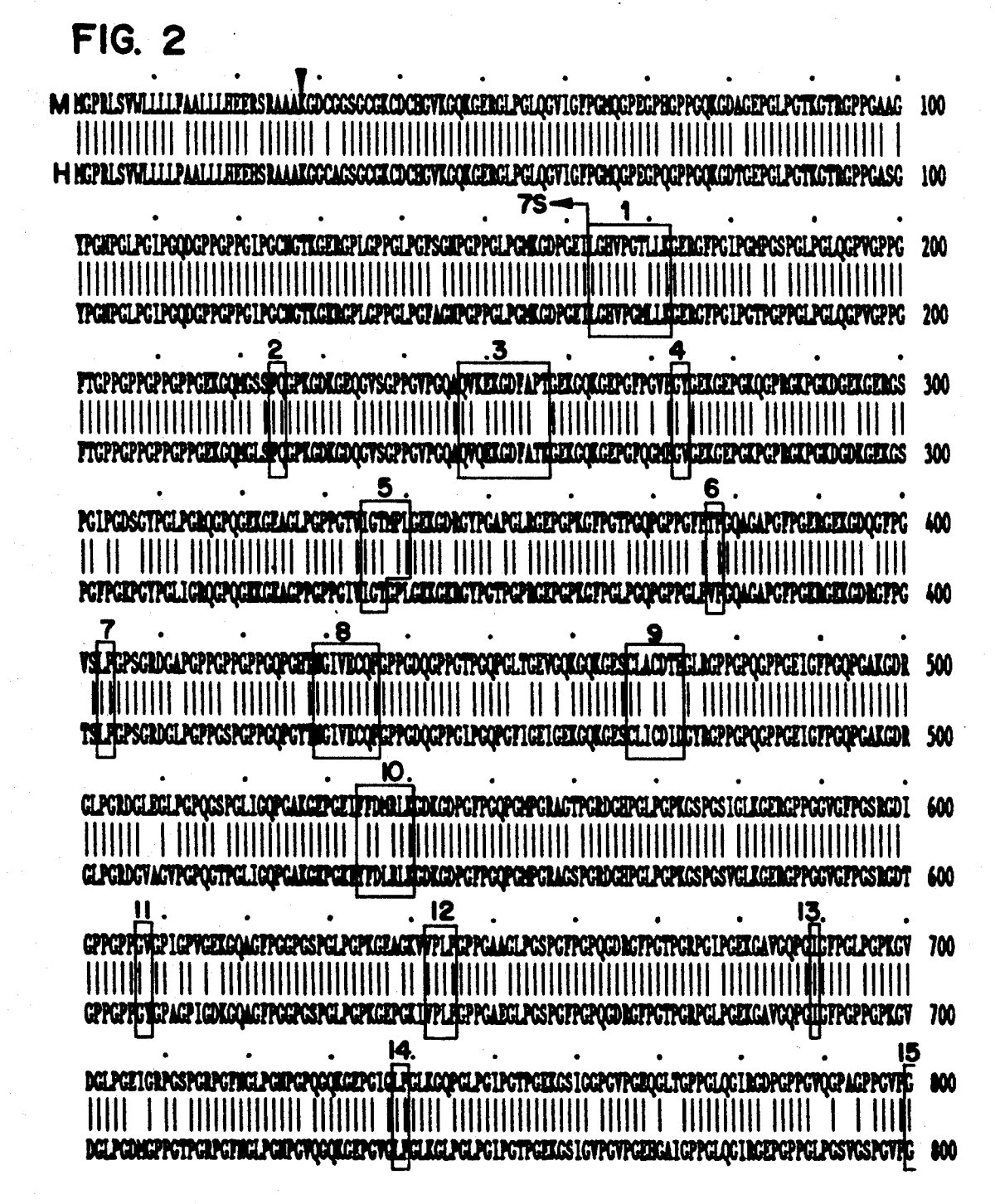

The structure of the two chains, the α1 and α2 chains of type IV collagen has been the subject of much study. See J. Oberbaümer et al., *Eur. J. Biochem.*, 147, 217–224 (1985); T. Pihlajanien et al., *J. Biol. Chem.*, 260, 7681–7687 (1985); U. Schwarz-Magdolen et al., *Febs. Lett.*, 208, 203–207 (1986); D. Brazel et al., *Eur. J. Biochem.*, 172, 35–42 (1988); R. Soininemi et al., *Febs. Lett.*, 225, 188–194 (1987); D. Brazel et al., *Eur. J. Biochem.*, 168, 529–536 (1987); G. Muthukamaran et al., *J. Biol. Chem.*, 264, 6310–6317 (1989); J. Saus et al., *J. Biol. Chem.*, 264, 6318–6324 (1989). The sequence of the α1 chain is shown in FIG. 2. Two copies of the α1 chain and one copy of the α2 chain are put together to make up the type IV collagen molecule. The total number of amino acids per collagen molecule is approximately 4,550. The α1(IV) chain contains about 1,645 amino acids.

Binding sites for heparin are of special interest since heparin-related macromolecules such as heparan sulfate proteoglycans are present in basement membranes and cell surfaces as well. Therefore, the association of these heparin-related molecules with type IV collagen may affect basement membrane structure and various cellular functions (such as adhesion, motility/migration, spreading, etc.).

Using criteria like (a) the hydropathy index of a sequence and (b) the number of lysine- and arginine residues present in a sequence, areas from the NC1 domain of the α1(IV) chain were selected and several peptides chemically synthesized. See U.S. Pat. No. 4,876,332. The ability of these peptides to bind to heparin was checked. However, this approach has several drawbacks: First, because of the very large number of amino acids present in type IV collagen, it is extremely time consuming and expensive to synthesize and test synthetic peptides fulfilling these criteria; Second, the hydropathy index of a sequence is not reliable.

IDENTIFICATION OF HEPARIN-BINDING SEQUENCES BY THE METHOD OF ROTARY SHADOWING AND ELECTRON MICROSCOPY

Figure 1:
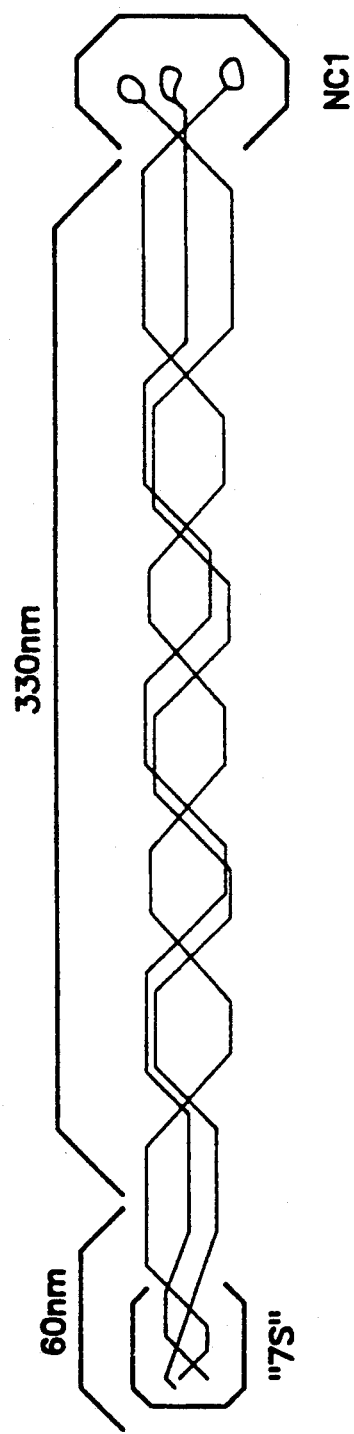
FIG. 1 is a diagrammatic representation of type IV collagen, indicating the structure of the $\alpha 1$(IV) and $\alpha 2$(IV) chains, each with a major non-collagenous, NC1 domain and the triple helix-rich domain containing interruption of the gly-X-Y triple helical motif.
Figure 3A:
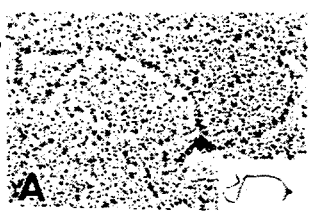
FIG. 3A-3F is a composite showing heparin molecules bound to type IV collagen molecules by the method of rotary shadowing.
Figure 3B:
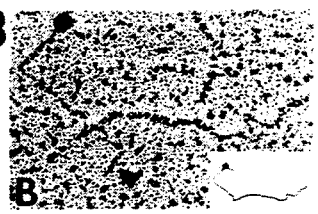
Figure 3C:
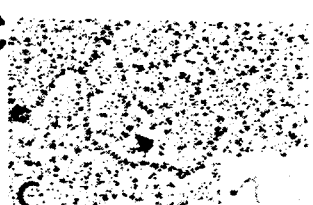
Figure 3D:
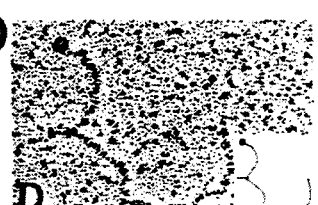
Figure 3E:
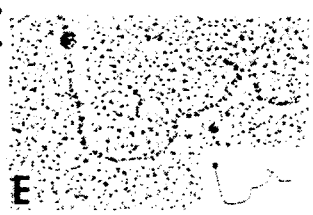
Figure 3F:
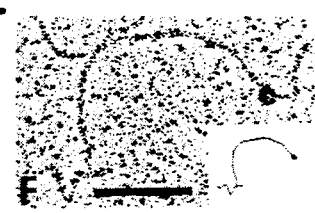
Figure 4:
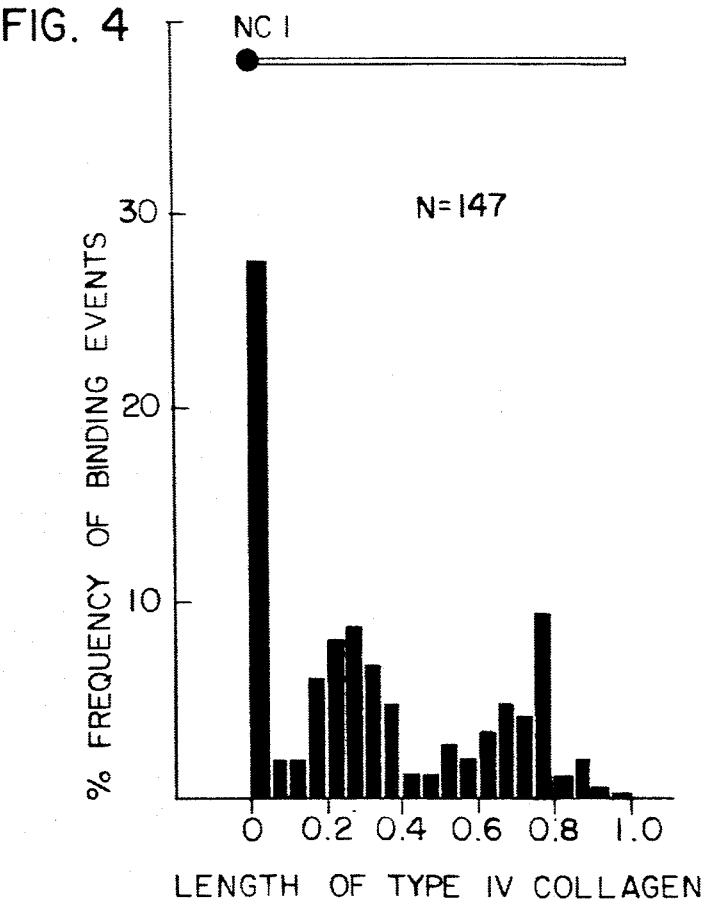
FIG. 4 is a histogram showing the distribution of heparin molecules to three distinctive sites along the length of type IV collagen, at the NC1 domain, and at 100 nm and 300 nm from the NC1 domain.

The technique of rotary shadowing-electron microscopy was used in order to map heparin-binding regions along the length of type IV collagen. This technique [Shotten et al., *J. Mol. Biol.*, 131, 303–325 (1979)] allows the direct observation of individual macromolecules, such as type IV collagen and heparin, for example. Because the molecules can be visualized to their full length in detail, it is also possible to map the site(s) of binding events between interacting molecules to distinctive/restricted domains. Therefore, type IV collagen was incubated with heparin at various molar ratios to allow interactions to occur between these two components, and then the distribution of these interactions was examined at the electron microscopic level. FIG. 3 is a composite showing a variety of such interactions. FIG. 4 is a histogram showing the distribution of a large number (147) of binding events of heparin along the length of type IV collagen. Statistical analysis indicated that this distribution was statistically significant ($p \leq 0.001$). This distribution indicated that one site for binding to heparin existed in the major non-collagenous NC1 domain, a second site was present at a distance of ≃100 nm from the NC1 domain, and a third site existed at a distance of ≃300 nm from the NC1 domain. This information was used to select peptides to be synthesized from the α1(IV) and α2(IV) chains of each of these three domains.

According to the present invention, peptide Hep-III was synthesized, which corresponds to residues 531–543 from the NH$_2$ end of α1(IV) located in the binding site 300 nm from the NC1 domain. This peptide was found to exhibit strong binding to heparin.

SYNTHESIS OF THE POLYPEPTIDE

The polypeptide of the invention was synthesized using the Merrifield solid phase method. This is the method most commonly used for peptide synthesis, and it is extensively described by J. M. Stewart and J. D. Young in *Solid Phase Peptide Synthesis*, Pierce Chemical Company, pub., Rockford, Ill. (2nd ed., 1984), the disclosure of which is incorporated by reference herein.

The Merrifield system of peptide synthesis uses a 1% crosslinked polystyrene resin functionalized with benzyl chloride groups. The halogens, when reacted with the salt of a protected amino acid will form an ester, linking it covalently to the resin. The benzyloxycarbonyl (BOC) group is used to protect the free amino group of the amino acid. This protecting group is removed with 25% trifluoroacetic acid (TFA) in dichloromethane (DCM). The newly exposed amino group is converted to the free base by 10% triethylamine (TEA) in DCM. The next BOC-protected amino acid is then coupled to the free amino of the previous amino acid by the use of dicyclohexylcarbodiimide (DCC). Side chain functional groups of the amino acids are protected during synthesis by TFA stable benzyl derivatives. All of these repetitive reactions can be automated, and the peptides of the present invention were synthesized at the University of Minnesota Microchemical facility by the use of a Beckman System 990 Peptide synthesizer.

Following synthesis of a blocked polypeptide on the resin, the polypeptide resin is treated with anhydrous hydrofluoric acid (HF) to cleave the benzyl ester linkage to the resin and thus to release the free polypeptide. The benzyl-derived side chain protecting groups are also removed by the HF treatment. The polypeptide is then extracted from the resin, using a 1.0M acetic acid, followed by lyophilization of the extract. Lyophilized crude polypeptides are purified by preparative high performance liquid chromatography (HPLC) by reverse phase technique on a C-18 column. A typical elution gradient is 0% to 60% acetonitrile with 0.1% TFA in $H_2O$. Absorbance of the eluant is monitored at 220 nm, and fractions are collected and lyophilized.

Characterization of the purified polypeptide is by amino acid analysis. The polypeptides are first hydrolyzed anaerobically for 24 hours at 110° C. in 6M HCl (constant boiling) or in 4N methanesulfonic acid, when cysteine or tryptophane are present. The hydrolyzed amino acids are separated by ion exchange chromatography using a Beckman System 6300 amino acid analyzer, using citrate buffers supplied by Beckman. Quantitation is by absorbance at 440 and 570 nm, and comparison with standard curves. The polypeptides may be further characterized by sequence determination. This approach is especially useful for longer polypeptides, where amino acid composition data are inherently less informative. Sequence determination is carried out by sequential Edman degradation from the amino terminus, automated on a Model 470A gas-phase sequenator (Applied Biosystems, Inc.), by the methodology of R. M. Hewick et al., *J. Biol. Chem.*, 256, 7990 (1981).

The invention will be further described by reference to the following detailed examples.

EXAMPLE 1

Heparin Binding to Plastic Plates Coated With Peptide Hep-III

Figure 5A:
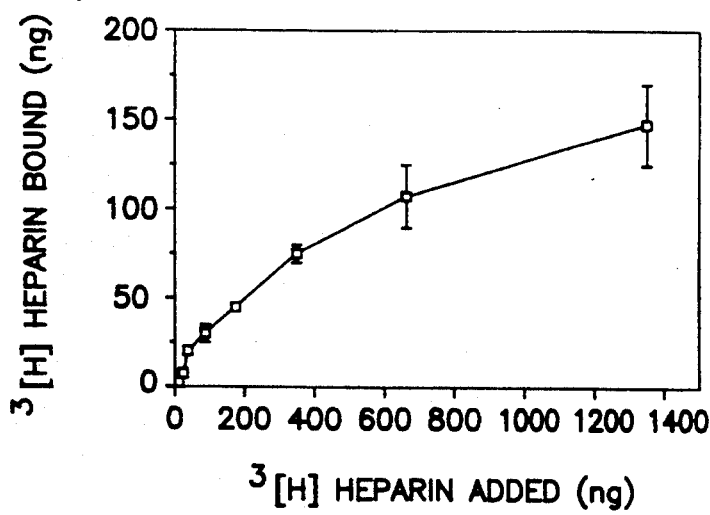
FIG. 5A is a graph showing the direct binding of increasing concentrations of heparin to peptide Hep-III coated on plastic substrates.
Figure 5B:
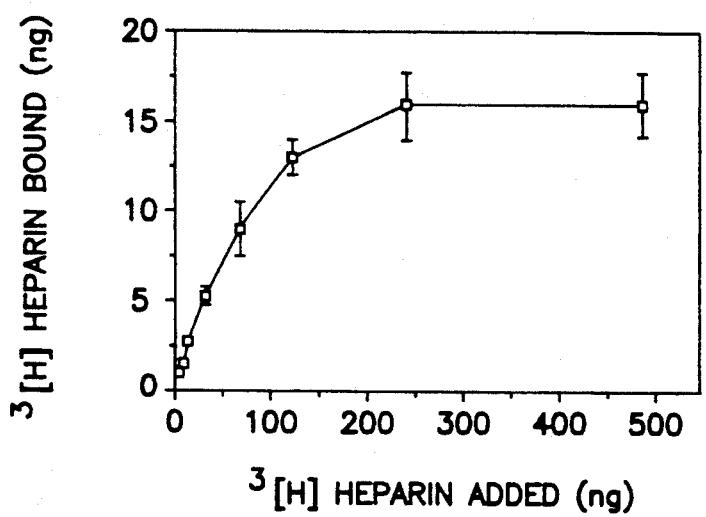
FIG. 5B is a graph showing the direct binding of increasing concentrations of heparin to peptide Hep-I (TS-2 in U.S. Pat. No. 4,876,332) coated on plastic substrates.
Figure 5C:
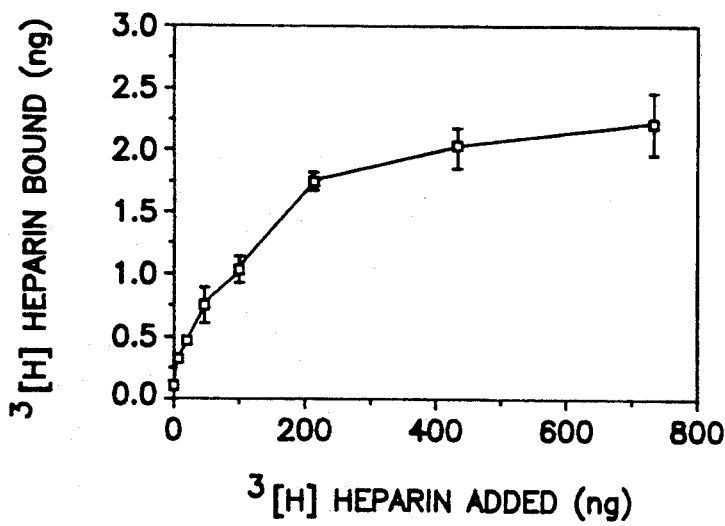
FIG. 5C is a graph showing the direct binding of increasing concentrations of heparin to type IV collagen coated on plastic substrates.

The ability of the synthesized peptide Hep-III to interact with heparin when coated on 96-well plastic plates was evaluated. Stock solutions of peptide Hep-III at a concentration of 500 µg/ml were prepared in phosphate-buffered saline containing 0.02% sodium azide. Fifty µl from each concentration was coated on the 96-well plates and left to dry overnight at 28° C. Then, wells were treated for two hours with 200 ml of 2 mg/ml BSA and 6 mM phosphate, 10 mM NaCl, 68 µM $CaCl_2$, pH 6.8 (wash buffer) in order to minimize non-specific binding. Next 50 µl of $^3$H-heparin (10 µg/ml) was added at increasing concentrations (0 to 1400 ng/well) for two hours at 37° C. The wells were then washed three times with wash buffer containing 0.05% Triton X-100 and finally they were incubated for thirty minutes at 60° C. with 200 µl of 0.5N NaOH and 1% SDS. The amount of $^3$H-heparin bound at each concentration was quantitated with a Beckman LS-3801 liquid scintillation counter. The results shown in FIG. 5 indicate that peptide Hep-III is a very potent binder of heparin. Comparison with data obtained using exactly the same methodology indicate that peptide Hep-III is at least 10 times stronger than peptide Hep-I (TS-2 in U.S. Pat. No. 4,876,332) (see FIG. 5B) and about 100 times stronger than type IV collagen, when used in the same coating concentrations. See FIG. 5C.

EXAMPLE 2

Inhibition of Heparin Binding to Type IV Collagen by Peptide Hep-III

Figure 6:
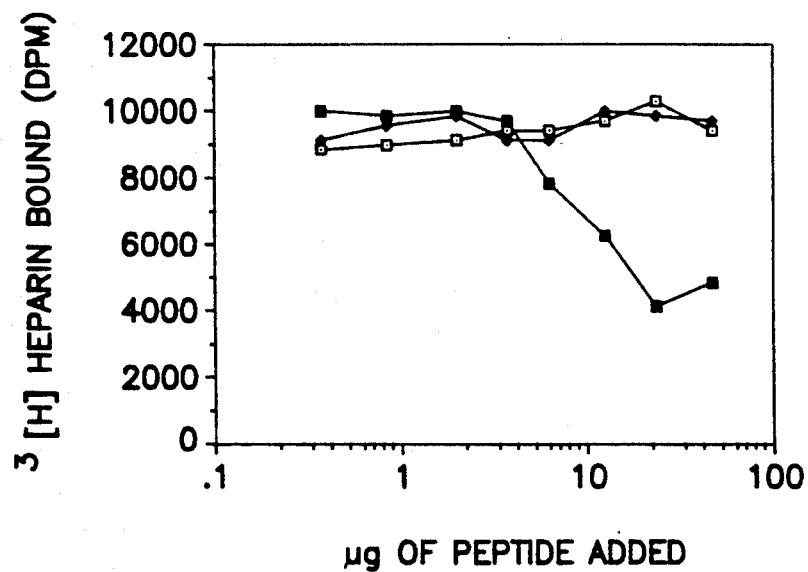
FIG. 6 is a graph showing the inhibition of the binding of heparin to the triple helix-rich domain of type IV collagen, by increasing concentrations of peptide Hep-III(■)[or control peptides 15(□)and 17(♦)] present in solution.

Peptide Hep-III in solution (and not absorbed to plastic), was screened for the ability to inhibit the binding of heparin to intact, native type IV collagen coated on plastic. This experimental approach avoids problems due to differential coating of peptides in heparin binding assays. Type IV collagen at 60 µg/ml in PBS was coated on 96-well plates, using 50 µl per well and dried overnight at 28° C. The wells were then treated for two hours with 2 mg/ml BSA in wash buffer (described above in Example 1). Peptide Hep-III at various dilutions ranging from 0.5 mg/ml to 5 µg/ml in PBS and CHAPS (cholamido-propyl-dimethyl-ammoniopropane-sulfonate) (a detergent used to avoid non-specific sticking) was co-incubated with a standard amount of $^3$H-heparin (500 ng per well 50 µg/ml final concentration) for two hours at 37° C. and the mixture was then transferred to the collagen coated plate (50 µl) and allowed to incubate for another two hours at 37° C. The wells were then washed and radioactivity was counted as described above. The results shown in FIG. 6 indicate that peptide Hep-III is a strong inhibitor of heparin binding to type IV collagen. These results also suggest that peptide Hep-III can bind to heparin not only when coated on plastic, but also when present in solution. Two other control peptides of similar length and hydropathy index (peptide 15 of the formula GHATEGPK and peptide 17 of the formula GPYDIIKGQP when tested with this assay were unable to compete for the binding of heparin to type IV collagen-coated plastic (FIG. 6).

EXAMPLE 3

Heparin/Peptide Interaction Specificity

Figure 7:
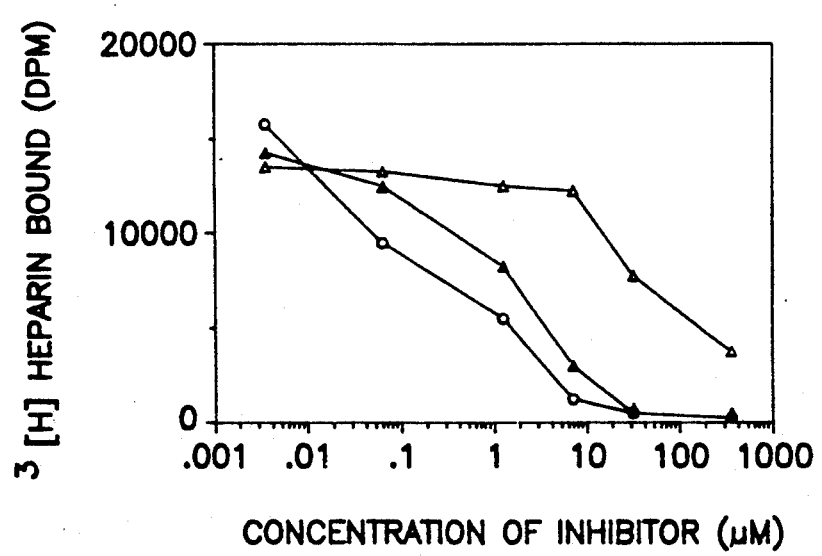
FIG. 7 is a graph depicting the competition of the binding of heparin to peptide Hep-III coated on plastic by various glycosoaminoglycans [heparin (○), dextran (▲) and chondroitin (△)] at increasing concentrations.

To check the specificity of the interaction between heparin and peptide Hep-III or whether the heparin structure was also critical to this interaction, heparin along with other sulfated glucosaminoglycans, dextran and chondroitin sulfate were used in competition experiments. A standard amount of 50 µg of a solution containing 500 µg/ml of peptide Hep-III was coated on 96-well plates as described above. Wells were treated for two hours with 2 mg/ml BSA in wash buffer. Then, a final volume of 50 µl was added to each well, containing a standard amount of $^3$H-heparin (50,000 cpm per well) and various amounts of non-radioactive heparin, dextran or chondroitin sulfate. After incubating for two hours at 37° C., the wells were washed and radioactivity was counted as described above in Example 1. FIG. 7 shows that unlabeled heparin is able to compete for the binding of tritiated heparin to peptide Hep-III at very low concentrations, whereas substantially more dextran is needed to achieve similar levels of competition and chondroitin sulfate cannot mimic this effect except at extremely high concentrations. These results suggest that not only the charge, but also the conformation of the glycosaminoglycan is crucial for this interaction.

EXAMPLE 4

Adhesion of Cancer Cells

Highly metastatic murmine melanoma cells, K-1735-M4 were originally provided by Dr. I. J. Fidler of Anderson Hospital, University of Texas Health Sciences Center, Houston, Tex. When the cells were received, a large number of early passage cells were propagated and frozen in liquid nitrogen. The tumor cells are usually cultured in vitro for no longer than six weeks. Following this period, the cells are discarded and new cells withdrawn from storage for use in further in vitro or in vivo experiments. This precaution is taken to minimize phenotypic drift that can occur as a result of continuous in vitro passage. The cells were cultured in Dulbecco's Modified Eagle's Medium containing 5% heat inactivated fetal calf serum. The cultures were grown in 37° C. incubators with a humidified atmosphere containing 5% $CO_2$. Cells were subcultured twice weekly by releasing cells gently from the flask, using 0.05% trypsin and 1 mM EDTA.

Figure 8A:
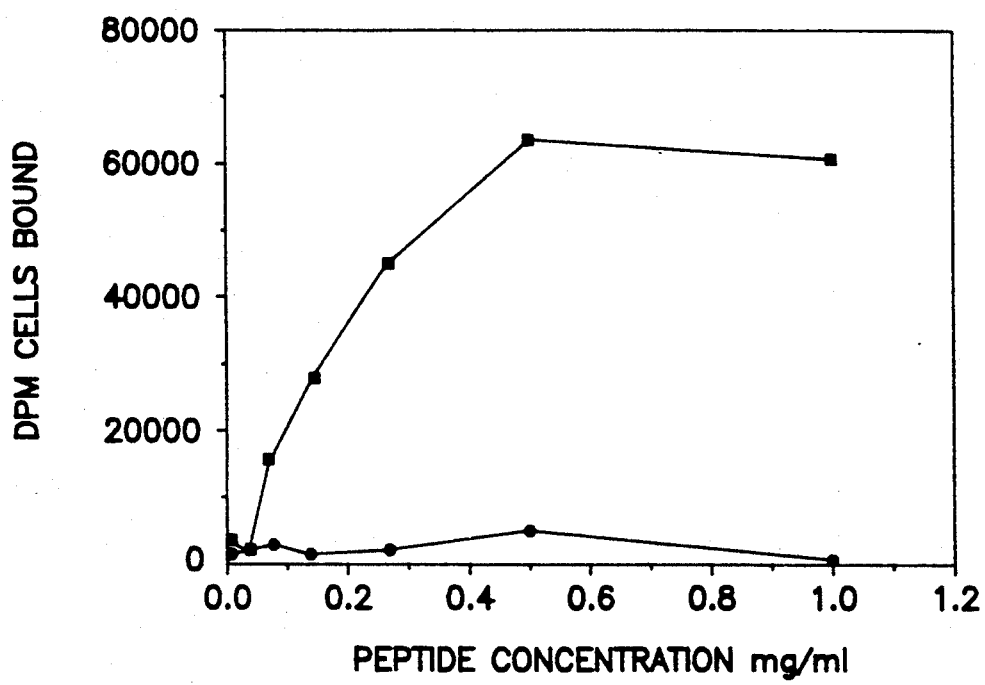
FIG. 8A is a graph depicting the direct binding of melanoma cells to peptide Hep-III (■), or control peptide ET-2 (●), coated onto plastic at increasing concentrations.

Cultures of cells which were 60–80% confluent were metabolically labeled for 24 hours with the addition of 3 mCi/ml of $^3$H-td (tritiated thymidine). On the day of the assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells adjusted to a concentration of $3-4 \times 10^4$/ml, and 100 μl of this cell suspension was added to the wells coated with peptide Hep-III at increasing concentrations. The assay mixture was then incubated at 37° C. for 120 minutes. At the end of the incubation, the wells were washed with warm PBS containing 10 mM $Ca^{++}$, and the adherent population was solubilized with 0.5N NaOH containing 1% sodium dodecyl sulfate. The solubilized cells were then quantitated using a liquid scintillation counter. As shown in FIG. 8A, increasing peptide concentrations produced a higher percentage of cell adhesion. Melanoma cell adhesion reached 80% of input at peptide concentrations of 0.5 μg/well. Maximal adhesion (70,000 dpm) corresponds to ≃70% of input which compares with that observed on to intact type IV collagen coated substrata. A control peptide (ET-2) (formula GDSRTITTKGERGQP) did not show any adhesion to peptide Hep-III.

EXAMPLE 5

Figure 9A:
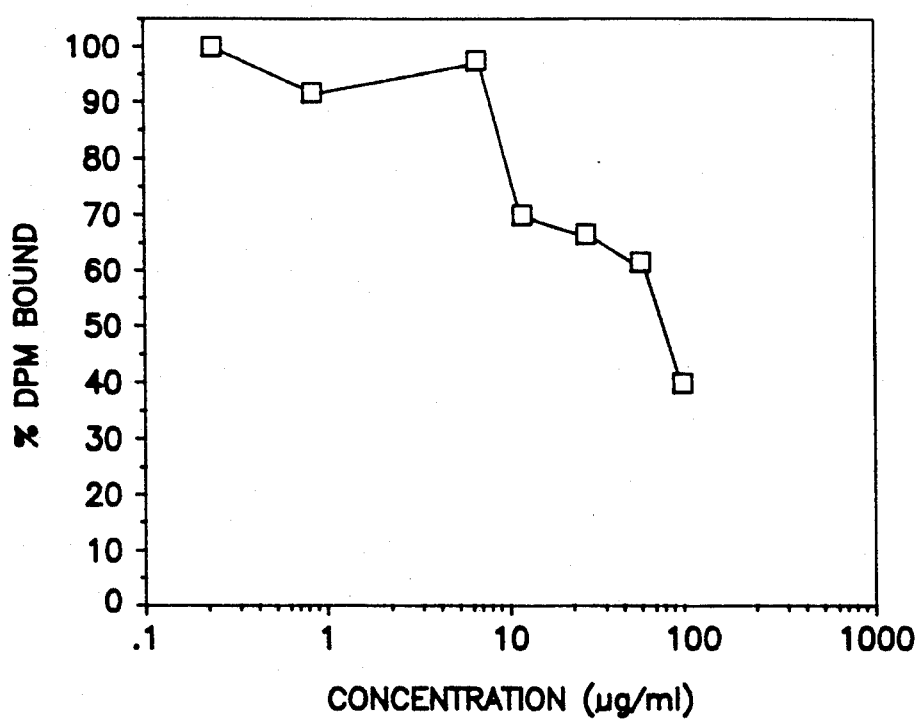
FIG. 9A is a graph depicting the competition of the binding of melanoma cells to type IV collagen coated substrata in the presence of peptide Hep-III in solution at increasing concentrations.

Inhibition of Adhesion of Cancer Cells in the Presence of Peptide Hep-III in Solution In order to test the ability of peptide Hep-III to demonstrate its function when present in solution, the melanoma cell line described above (M4) was used. Cells were grown, labeled and harvested as described in Example 4, but after detachment and washing they were coincubated for 20 min. in the presence of various concentrations of peptide Hep-III in solution. They were then applied for another 20 min. on type IV collagen-coated plastic wells. At the end of the incubation the same treatment described in Example 4 was used. As shown in FIG. 9A, increasing concentrations of peptide Hep-III were able to dramatically decrease the binding of melanoma cells to type IV collagen-coated substrata.

EXAMPLE 6

Hep-III in the Adhesion of Endothelial Cells

A. Isolation of Bovine Aortic Endothelial Cells

Figure 8B:
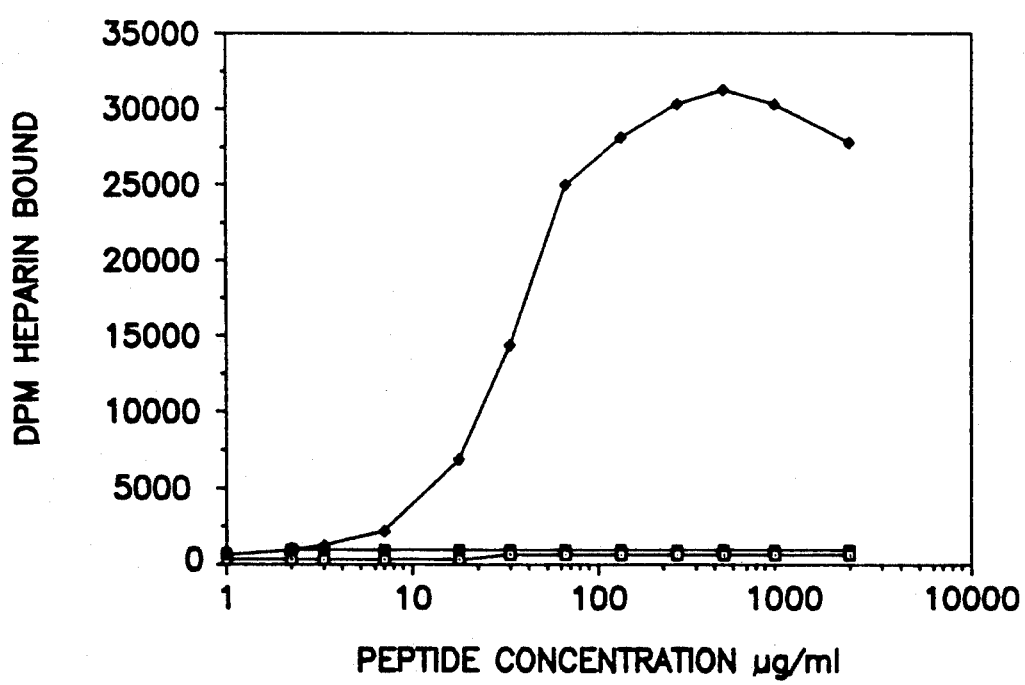
FIG. 8B is a graph depicting the direct binding of aortic endothelial cells to peptide Hep-III (♦), control peptide ET-2 (■) and BSA (□), coated onto plastic at increasing concentrations.

Bovine aortic endothelial cells were isolated according to the following protocol. Aortas were obtained from a local slaughterhouse, washed in cold phosphate buffered saline (PBS) (136 mM NaCl, 2.6 mM KCl, 15.2 mM $Na_2HPO_4$, pH 7.2) and processed within 2 hours. Crude collagenase (CLS III, 125–145 units per mg dry weight, Cooper Biomedical) was used at 2 mg/ml in Dulbecco's modified Eagle's medium (DMEM) (GIBCO). The vessel was clamped at the distal end, filled with the collagenase-PBS solution and digestion was carried out for 10 minutes. The lumenal contents were harvested, followed by the addition of fresh collagenase for two additional 10-minute periods. The enzyme-cell suspensions were added to an equal volume of DMEM containing 10% fetal bovine serum (FBS) to inhibit the enzyme and spun in a centrifuge at 400×g for 10 minutes. The resulting cell pellet was resuspended in DMEM containing 10% FBS, 100 units/ml of penicillin G, 100 μg/ml of streptomycin and 100 μg/ml of crude fibroblast growth factor. Cells are in 75 cm$^2$ flasks in a humidified 5% $CO_2$ atmosphere at 37° C. Cultures were fed twice a week with the same medium and cells were used in assays when approximately 75% confluent. The cells were labeled for 24 hours prior to use with a mixture of $^{35}$S-labeled amino acids (3 mCi). Cells were identified as endothelial in nature by characteristic cobblestone morphology, contact inhibition of growth upon reaching confluency, and positive immunofluorescent staining for factor VIII:RAg (Miles Laboratories) [Schwartz, In Vitro, 14, 966 (1978)]. Only endothelial cells, megakaryocytes and platelets are known to contain the factor VIII:RAg. This method routinely gives a high yield of endothelial cells with little contamination (less than 5%) by smooth muscle cells, pericytes or fibroblasts as judged by phase contrast microscopy as well as by immunostaining. Direct adhesion of endothelial cells was performed as discussed in Example 4. Plastic substrates were coated with increasing concentrations of peptide Hep-III and a constant number of $^{35}$S-labeled cells were added per well and they were incubated for 120 min. at 37° C. Subsequently, the wells were treated as discussed in Example 4. Peptide Hep-III promotes substantial adhesion of endothelial cells even at very low plating concentrations (20 μg/ml) (FIG. 8B). Maximal adhesion (≃30,000 dpm) corresponds to ≃60% of input cells and is comparable with adhesion of these cells onto intact type IV collagen-coated substrates. BSA and a control peptide (ET-2) (formula GDSRTITTKGERGQP) did not show any significant adhesion.

B. Inhibition of Adhesion of Bovine Aortic Endothelial Cells to Type IV Collagen by Peptide Hep-III Inhibition of adhesion was measured using 96-well microtiter plates. In each well 50 μl of a type IV collagen solution at 60 μg/ml were absorbed by incubating overnight at 29° C.

Figure 9B:
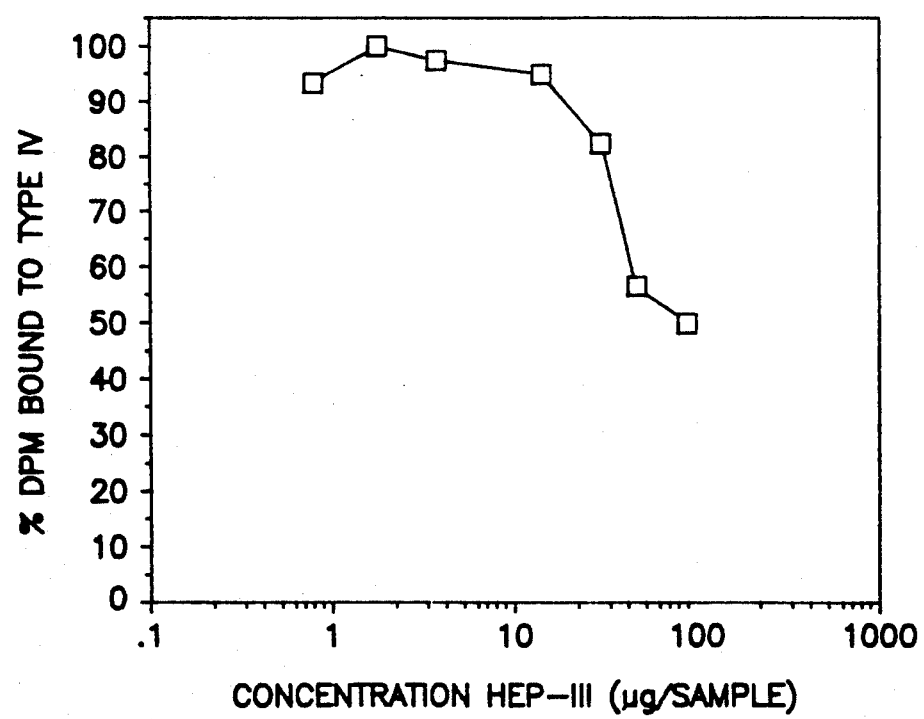
FIG. 9B is a graph depicting the competition of the binding of endothelial cells, to type IV collagen coated substrata in the presence of peptide Hep-III in solution at increasing concentrations.

Cultures of cells which were 60-80% confluent were metabolically labeled for 24 hours with the addition of mCi/ml of $^{35}$S-amino acid mixture. On the day of assay, the cells were harvested by trypsinization, the trypsin was inhibited by the addition of serum, and the cells were washed free of this mixture and resuspended in DMEM buffered with HEPES at pH 7.2. The adhesion medium also contained 2 mg/ml BSA. The cells were adjusted to a concentration of $3-4 \times 10^4$/ml, and 50 $\mu$l of this cell suspension was added to 50 $\mu$l of increasing concentrations of peptide Hep-III in the same buffer at 37° C. After 15 min. of co-incubation, 50 $\mu$l of the mixture was applied to the type IV collagen coated wells for 20 min. at 37° C. At the end of the incubation, the wells were washed with warm PBS containing 10 mM Ca++, and the adherent population was solubilized with 0.5N NaOH containing 1% sodium dodecyl sulfate. The solubilized cells were then quantitated using a liquid scintillation counter. Each determination was done in triplicate. The results of this study are summarized in FIG. 9B. (Average Total DPM added: 91220; % Bound at Maximal Adhesion: 39%).

EXAMPLE 7

A. Direct Binding of $^{125}$I-Labeled Peptide Hep-III to Cell Surfaces

Figure 10A:
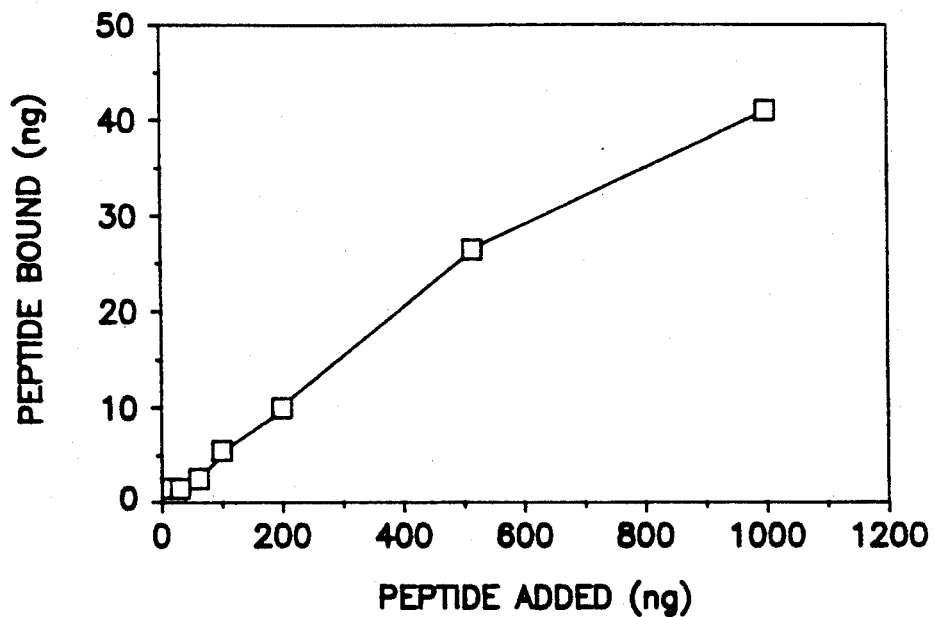
FIG. 10A is a graph depicting the direct binding of increasing concentrations of iodinated ($^{125}$I-labeled) peptide Hep-III to the surface of melanoma cells.
Figure 10B:
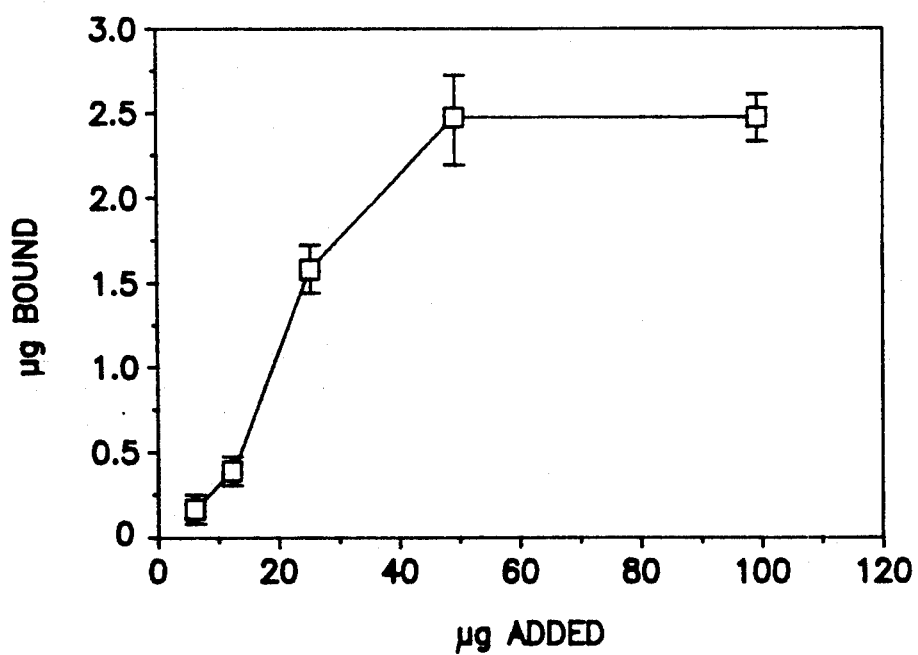
FIG. 10B is a graph depicting the direct binding of increasing concentrations of iodinated ($^{125}$I-labeled) peptide Hep-III to the surface of endothelial cells.

Endothelial and melanoma cells were grown in culture as described in Examples 4, 5, and 6 (supra). Cells used for this type of experiment were not labeled with radioactivity. Unlabeled cells were harvested by trypsinization (supra) on the day of the experiment. About 5,000 cells were mixed with 50 $\mu$l of a given concentration of peptide Hep-III in solution. Increasing concentrations of peptide Hep-III were used. The cells were incubated with the iodinated peptide for 15 min. at 4° C. and they were then pelleted by centrifugation. The cells were then resuspended and washed 3 times with DMEM containing 2 mg/ml BSA and 50 mM Hepes. Following the washes, the cells were pelleted for a final time in plastic tubes, the supernatant was decanted and the radioactivity of the pellet was quantitated in a Beckman scintillation counter. The binding of peptide Hep-III to endothelial cells is saturable (FIG. 10B)—an indication of specificity. Peptide Hep-III also binds to the surface of melanoma cells (FIG. 10A) with a tendency for saturation at the higher concentrations used. These experiments indicate that peptide Hep-III specificity interacts with the surfaces of both endothelial cells and melanoma.

Figure 11A:
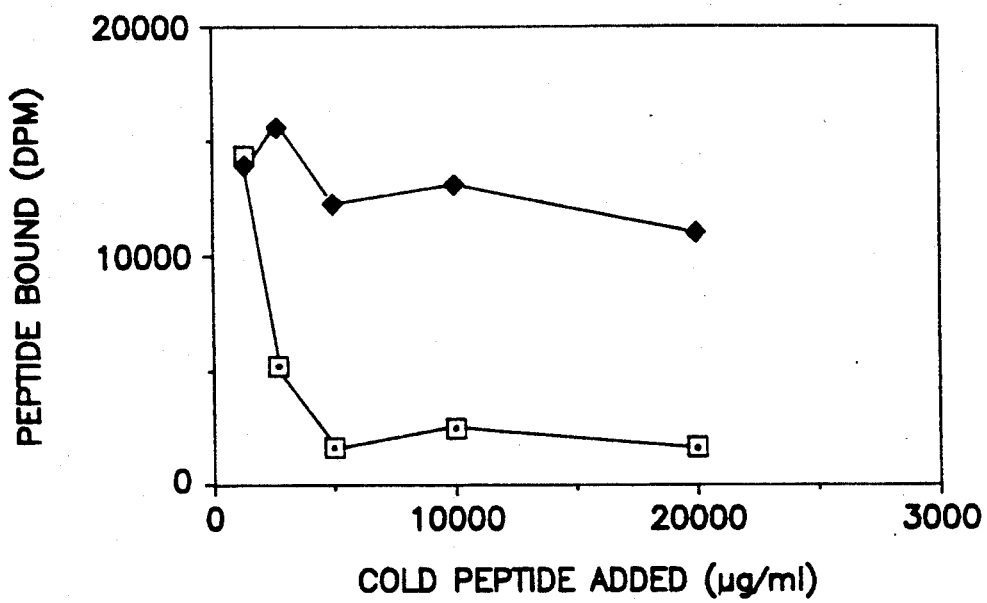
FIG. 11A is a graph depicting the competition of the binding of iodinated peptide Hep-III (□), and control peptide 15 (▲), to melanoma cells in the presence of increasing concentrations of unlabeled Hep-III.
Figure 11B:
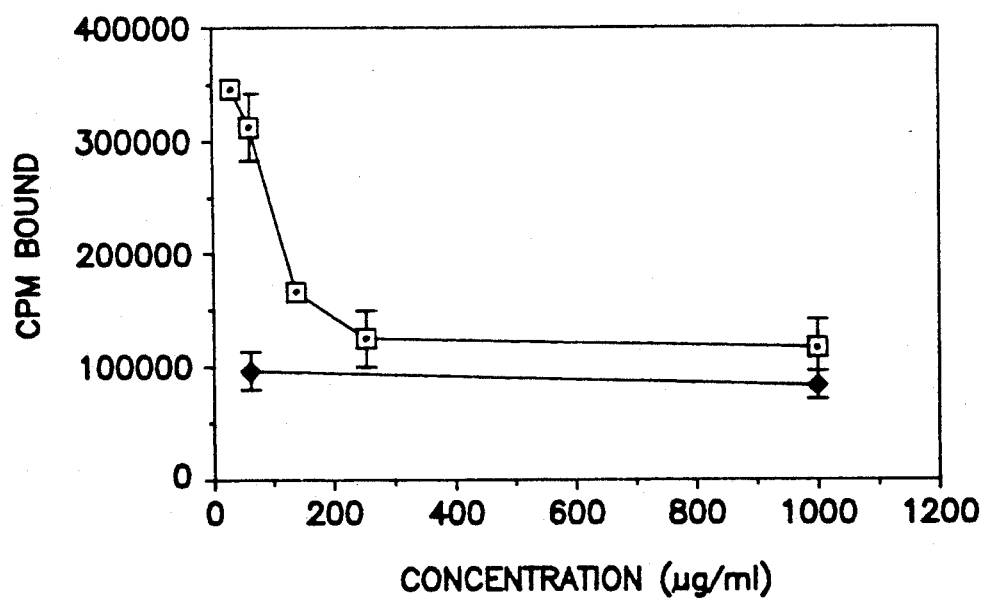
FIG. 11B is a graph depicting the competition of the binding of iodinated peptide Hep-III (□), and control peptide ET-2 (♦) to endothelial cells in the presence of increasing concentrations of unlabeled Hep-III.

B. Inhibition of the Binding of $^{125}$I-Labeled Peptide Hep-III to the Cell Surface by an Excess of Unlabeled Peptide Melanoma and endothelial cells were grown in culture as discussed in Examples 4, 5, 6, and 7A (supra). On the day of the experiment, the cells were harvested by trypsinization (supra) and were co-incubated with 50 $\mu$l of peptide Hep-III. 50 $\mu$l a constant amount of $^{125}$I-labeled peptide Hep-III was mixed with increasing concentrations of unlabeled peptide Hep-III or a control peptide (maximal excess of unlabeled peptide: 500-fold over radiolabeled Hep-III). 50 $\mu$l of each concentration of unlabeled peptide which was mixed with radiolabeled Hep-III were then added to cells in suspension (5,000 cells per concentration of peptide). The cells were incubated with the mixture of unlabeled-radiolabeled peptide for 15 min. at 4° C. and they were then pelleted. The cells were subsequently washed and bound radioactivity was quantitated as described in Example 7A. FIG. 11A shows that the binding of radiolabeled Hep-III to the surface of melanoma cells can be competed only by an excess of unlabeled peptide Hep-III, whereas control (negative) peptide 15 (formula GHATEGPK) failed to compete; a similar competition can be observed for the binding of labeled peptide Hep-III to the surface of endothelial cells (FIG. 11B). Again, an excess of unlabeled peptide Hep-III could efficiently compete for the binding of radiolabeled Hep-III, but control peptide ET-2 (formula GDSRTITT-KGERGQP) failed to compete. These experiments provide confirmation that a specific interaction occurs between melanoma and endothelial-cell surfaces and peptide Hep-III.

These results taken together indicate that peptide Hep-III is a major participant in the process of endothelial cell adhesion.

A number of practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft, which is generally woven or knitted from nitrocellulose or polyester fiber, particularly Dacron ™ (polyethylene terephthalate) fiber. Most types of cells are attracted to type IV collagen and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumas, e.g., spinal cord injuries.

In such cases, it may be advantageous to couple the peptide to a biological molecule, such as collagen, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, the polypeptides of the present invention can be used to promote cell adhesion of various cell types to naturally occurring or artificial substrata intended for use in vitro. For example, a culture substrate such as the wells of a microtiter plate or the medium contacting surface of microporous fibers or beads, can be coated with the cell-attachment polypeptides. This can obviate the use of type IV collagen in the medium, thus providing better defined conditions for the culture as well as better reproducibility.

As one example of commercial use of cell attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of coating protein in the growth medium and the present polypeptides are expected to provide an improved, chemically defined coating for such purposes. Other surfaces or materials may be coated to enhance attachment, such as glass, agarose, synthetic resins or long-chain polysaccharides.

In the past, selected laminin domains have been studied for ability to decrease the metastatic potential of invasive cell lines [McCarthy et al., *Cancer Met. Rev.*, 4, 125–152 (1985)]. This effect is mediated via the saturation and therefore neutralization of cell surface receptors for laminin. In accordance with the present invention, the data presented herein suggest that receptors for the polypeptide Hep-III from type IV collagen should exist on cell surfaces of malignant cells. Consequently, this polypeptide could be used to block type IV collagen receptors of metastatic cells and therefore reduce their metastatic potential. In addition, peptide Hep-III could be used to enhance re-epithelialization of various transplants, like corneal transplants, etc.

The invention has been described with reference to various specific and preferred embodiments and techniques. However, it should be understood that many variations and modifications may be made while remaining within the spirit and scope of the invention.

What is claimed is:

1. A prosthetic device designed for placement in vivo, comprising a surface coated with a composition comprising a polypeptide of the formula:

gly-glu-phe-tyr-phe-asp-leu-arg-leu-lys-gly-asp-lys.

2. The prosthetic device of claim 1, wherein said surface constitutes a portion of a vascular graft.

3. The prosthetic device of claim 1, wherein said surface is made of a synthetic resin fiber.

4. The prosthetic device of claim 1, wherein said surface constitutes a portion of an intraocular contact lens.

5. The prosthetic device of claim 1, wherein said surface constitutes a portion of a hip replacement implant.

6. The prosthetic device of claim 1, wherein said surface constitutes a portion of a percutaneous device.

7. A prosthetic device in accordance with claim 3, wherein said synthetic resin fiber is selected from the group consisting of nitrocellulose or polyester.

8. A prosthetic device in accordance with claim 3, wherein said synthetic resin fiber is a polyethylene terephthalate.

* * * * *

UNITED STATES PATENT AND TRADEMARK OFFICE
CERTIFICATE OF CORRECTION

PATENT NO. : 5,152,784           Page 1 of 2

DATED : October 6, 1992

INVENTOR(S) : Photini-Effie C. Tsilibary

It is certified that error appears in the above-identified patent and that said Letters Patent is hereby corrected as shown below:

At column 2, line 62, for "Fig." read --Figs.--

At column 3, line 14, for "(□)" read --(▣)--

At column 3, line 26, for "(□)" read --(▣)--

At column 3, line 44, for "(□)" read --(▣)--

At column 3, line 48, for "(□)" read --(▣)--

At column 3, line 45, for "(▲)" read --(◆)--

At column 4, line 47, for "($p \leq 0.001$.)" read --($p \leq 0.001$)--

At column 4, line 67, for "Ill" read --IL.--

At column 5, line 26, for "1.0M" read --1.0 M--

At column 5, line 35, for "6M HCl" read --6 M HCl--

At column 5, line 36, for "4N" read --4 N--

At column 6, line 5, for "0.5N" read --0.5 N--

At column 7, line 45, for "0.5N" read --0.5 N--

At column 8, line 8, after "Example 6" insert --Effect of Peptide--

At column 8, line 30, after "are" insert --cultured--

UNITED STATES PATENT AND TRADEMARK OFFICE
CERTIFICATE OF CORRECTION

PATENT NO. : 5,152,784

DATED : October 6, 1992

INVENTOR(S) : Photini-Effie C. Tsilibary

It is certified that error appears in the above-identified patent and that said Letters Patent is hereby corrected as shown below:

Col. 9, line 3, after "of" insert --3--

Col. 9, line 17, for "0.5N" read --0.5 N--

Signed and Sealed this

Twenty-first Day of December, 1993

Attest:

BRUCE LEHMAN

Attesting Officer

Commissioner of Patents and Trademarks